United States Patent
Neumann et al.

(10) Patent No.: US 6,919,487 B2
(45) Date of Patent: *Jul. 19, 2005

(54) BIS(4-HYDROXYARYL)ALKANES

(75) Inventors: Rainer Neumann, Krefeld (DE); Rolf Lanze, Krefeld (DE); Frieder Heydenreich, Düsseldorf (DE); Michael Bödiger, League City, TX (US); Michael Prein, Brasschaat (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/149,906

(22) PCT Filed: Dec. 7, 2000

(86) PCT No.: PCT/EP00/12324

§ 371 (c)(1),
(2), (4) Date: Jun. 17, 2002

(87) PCT Pub. No.: WO01/46104

PCT Pub. Date: Jun. 28, 2001

(65) Prior Publication Data

US 2002/0183562 A1 Dec. 5, 2002

(30) Foreign Application Priority Data

Dec. 20, 1999 (DE) .......... 196 61 566

(51) Int. Cl.$^7$ .............. C07C 37/68

(52) U.S. Cl. ............. 568/724

(58) Field of Search ........ 568/724

(56) References Cited

U.S. PATENT DOCUMENTS

| | | | | |
|---|---|---|---|---|
| 3,936,507 A | * | 2/1976 | Ligorati | |
| 4,294,994 A | * | 10/1981 | Li | |
| 4,371,691 A | * | 2/1983 | Friedhofen | |
| 4,931,146 A | * | 6/1990 | Iimuro | |
| 5,382,711 A | * | 1/1995 | Asaoka | |
| 5,629,457 A | | 5/1997 | Zhang et al. | 568/724 |
| 5,696,295 A | * | 12/1997 | Wulff | |
| 5,783,733 A | * | 7/1998 | Kissinger | |
| H1943 H | * | 2/2001 | Kissinger | |
| 6,384,288 B1 | * | 5/2002 | Kuhling | |
| 6,414,198 B1 | * | 7/2002 | Lanze | |
| 2003/0055296 A1 | * | 3/2003 | Kissinger | |

FOREIGN PATENT DOCUMENTS

| | | | |
|---|---|---|---|
| DE | 198 48 026 | | 4/2000 |
| EP | 343349 | * | 11/1980 |
| WO | WO-00/39060 | * | 7/2000 |

* cited by examiner

Primary Examiner—Michael L. Shippen
(74) Attorney, Agent, or Firm—Joseph C. Gil; Aron Preis

(57) ABSTRACT

The present application relates to a process for producing high-purity bis(4-hydroxyaryl)alkanes from adducts of bis(4-hydroxyaryl)alkanes and aromatic hydroxy compounds, which are obtained by acid-catalysed reaction of the aromatic hydroxy compounds with ketones.

7 Claims, 1 Drawing Sheet

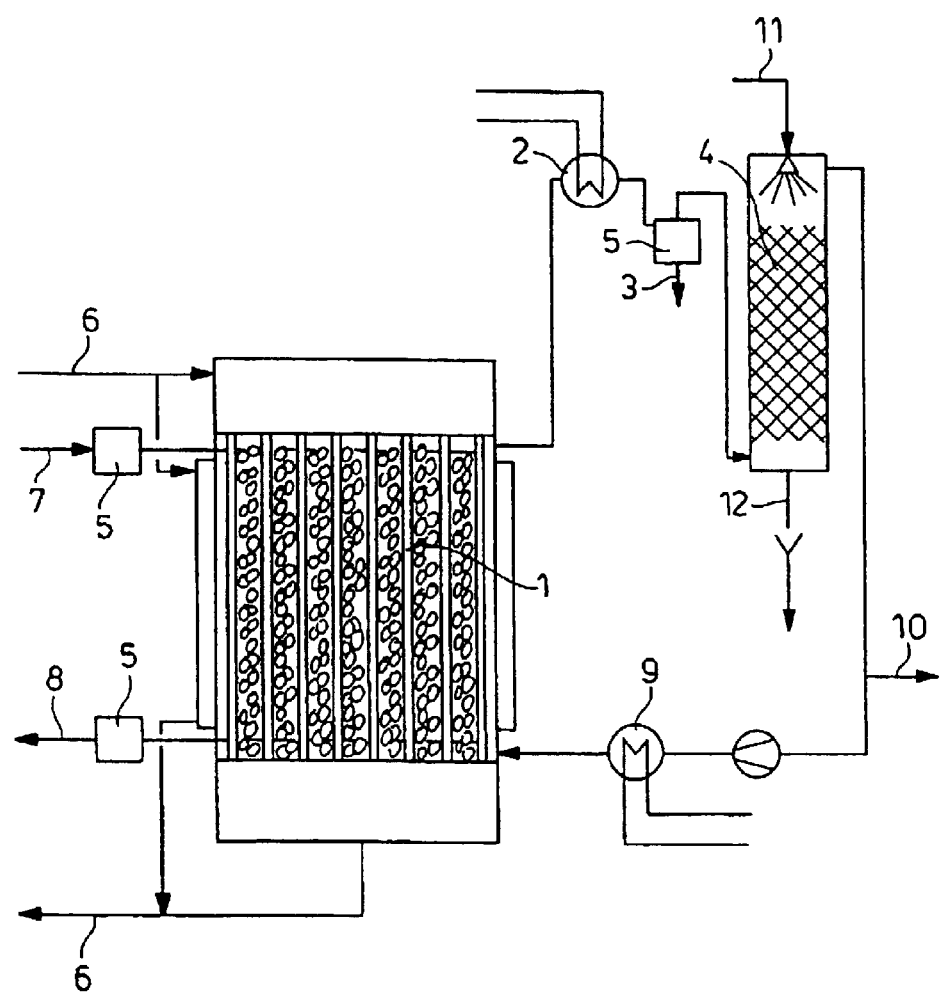

BIS(4-HYDROXYARYL)ALKANES

The present application relates to a process for producing high-purity bis(4-hydroxyaryl)alkanes from adducts of bis(4-hydroxyaryl)alkanes and aromatic hydroxy compounds, which are obtained by acid-catalysed reaction of the aromatic hydroxy compounds with ketones.

Bisphenols, as condensation products of phenols and carbonyl compounds, constitute starting materials or intermediate products for the production of a wide range of commercial products. Of particular industrial significance is the condensation product from the reaction between phenol and acetone, 2,2-bis(4-hydroxyphenyl)propane (BPA). BPA serves as the starting material for the production of various polymeric materials such as, for example, polyarylates, polyetherimides, polysulfones and modified phenol-formaldehyde resins. It is preferably used in the production of epoxy resins and polycarbonates.

Industrially relevant BPA production methods arc known and are based on the acid-catalysed reaction of phenol and acetone, wherein a phenol-acetone ratio preferably greater than 5:1 is established in the reaction. The acid catalysts used may comprise both homogeneous and heterogeneous Brønsted or Lewis acids, such as for example strong mineral acids such as hydrochloric or sulfuric acid. Gel-form or macroporous sulfonated cross-linked polystyrene resins (acidic ion exchangers) are preferably used.

When phenol is reacted with acetone in the presence of acid catalysts, a product mixture arises which primarily contains BPA and water, in addition to unreacted phenol and optionally acetone. In addition typical condensation reaction by-products arise in small quantities, such as for example 2-(4-hydroxyphenyl)-2-(2-hydroxyphenyl)propane (o,p-BPA), substituted indans, hydroxyphenyl indanols, hydroxyphenyl chromans, substituted xanthenes and more highly condensed compounds having three or more phenyl rings in the molecular framework.

The above-mentioned by-products, as well as water, phenol and acetone, impair the suitability of BPA for the production of polymers and have to be separated off by suitable processes. High purity levels are required of the raw material BPA in particular in the production of polycarbonate.

One method of working up and purifying BPA entails the separation of BPA from the reaction mixture in the form of an approximately equimolar crystalline adduct with phenol by cooling of the reaction mixture, with the BPA/phenol adduct being crystallised as a crystal suspension. The BPA/phenol adduct crystals are then separated from the liquid phase by a suitable apparatus for solid/liquid separation, such as a rotary filter or centrifuge, and fed to a further purification stage.

Adduct crystals thus obtained typically exhibit a purity of >99% BPA relative to the minor constituents with a phenol content of approximately 40%. By washing with suitable solutions, which typically contain one or more components from the group comprising acetone, water, phenol, BPA and minor constituents, the adduct crystals may be relieved of contaminants adhering to the surface.

The liquid stream (mother liquor) arising during solid/liquid separation contains phenol, BPA, water arising during the reaction, unreacted acetone and has an increased content of the minor constituents typically arising during BPA production. This mother liquor stream is fed back into the reaction unit. In order to maintain the catalytic activity of the acid ion exchangers, water which arose previously is removed by distillation, wherein acetone which may still be present is also removed from the mother liquor. The dewatered reaction stream thus obtained is replenished with phenol and acetone and fed back into the reaction unit. Alternatively, water and acetone may also be removed wholly or in part by distillation prior to performing suspension crystallisation of the BPA phenol adduct. During the above-mentioned distillation steps, some of the phenol present in the reaction solution may also be separated off by distillation.

One problem associated with such a recirculation method is that the contents of by-products of BPA production are increased in the recirculated stream and lead to deactivation of the catalyst system. In order to prevent excessive accumulation of minor constituents in the recirculated stream, some of the recirculated stream is removed from the process chain as so-called BPA resin, optionally after partial or complete recovery of phenol by distillation.

In addition, it has proven advantageous to pass part or all of the recirculated stream through a rearrangement unit filled with acid ion exchanger after solid/liquid separation and before or after the separation of water and residual acetone. This unit is generally operated at higher temperatures than the reaction unit. In this rearrangement unit, some of the minor constituents of BPA production present in the recirculated stream are isomerised to form BPA, such that the total BPA yield may be increased.

The BPA/phenol adduct crystals obtained subsequent to the above-described suspension crystallisation of the reaction solution and solid/liquid separation are fed to further purification stages, wherein separation of phenol and optionally a reduction in the concentration of minor constituents is achieved.

Thus, the adduct crystals of phenol, organic solvents, water or mixtures of the above-mentioned solvents may be recrystallised by suspension crystallisation. By selecting suitable solvents, it is also possible to separate off wholly or in part the phenol present in the adduct crystals. The phenol which may remain in the BPA after recrystallisation is then separated off completely by suitable methods involving distillation, desorption or extraction.

Alternatively, the phenol may also be removed from the adduct crystals by melting processes. However, during these processes, the BPA is subject to elevated temperatures, which results in unwanted BPA dissociation.

The object was therefore an optimised process for separating adducts of bis(4-hydroxyaryl)alkanes and aromatic hydroxy compounds, in which the bis(4-hydroxyaryl)alkanes (bis(4-hydroxyaryl)alkane/arylhydroxy adducts) are obtained in highly pure form.

It has now been found that this object may be achieved by a special arrangement and procedure.

The invention therefore provides the use of a desorber (1) with a distillation unit optionally connected upstream for separating bis(4-hydroxyaryl)alkanes from bis(4-hydroxyaryl)alkane/arylhydroxy adducts.

Using this device, bis(4-hydroxyaryl)alkane/arylhydroxy adducts may be melted under product-protective conditions and separated from the aromatic hydroxy compounds.

In a preferred embodiment, 2,2-bis(4-hydroxyphenyl)propane is separated off from 2,2-bis(4-hydroxyphenyl)propane/phenol adducts in the desorber (1).

Desorption is performed in the desorber (1). The phenol is separated off and the final BPA product is obtained as a bottom product. The desorber (1) preferably consists of tube bundle heat exchangers. These tube bundle heat exchangers are in particular arranged upright and provided at their lower part with a number of nozzles, via which a hot inert gas, in particular nitrogen, is introduced. The gas is preferably recirculated. The heat exchanger is heated (6) by tubes and via the outer jacket. The spaces between the heat exchanger tubes are filled on the product side with ceramic spheres (steatite). The product chamber of the desorber is mainly filled with liquid.

The phenol, once distilled off, arrives with the gas at condensers (2) and is then fed to the phenol collecting receiver (3).

The gas leaving the condensers (2) and separators (3) is preferably cleaned in a scrubbing tower (4) and optionally a filter (5) and pumped back into the desorber via compressors.

To maintain a low oxygen content in the recirculated stream, make-up gas is preferably supplied constantly.

The invention also provides a process for separating bis(4-hydroxyaryl)alkanes from adducts of bis(4-hydroxyaryl)alkanes having aromatic hydroxy compounds, which is characterised in that the crystallised, filtered-off and purified bis(4-hydroxyaryl)alkane/arylhydroxy adducts arising during the process are melted under product-protective conditions and separated by distillation and/or desorption from the aromatic hydroxy compounds.

Separation is preferably performed in such a way that the value of the aromatic hydroxy compounds lies below 50 ppm.

In a preferred embodiment, 2,2-bis(4-hydroxyphenyl)propane is separated off from 2,2-bis(4-hydroxyphenyl)propane/phenol adducts.

Separation is preferably performed by desorption, optionally preceded by distillation.

A mixed crystal melt with a phenol content of from 40 to 5%, preferably 20 to 10%, particularly preferably 15 to 10%, is preferably fed to the desorber.

The temperature of the melt in the desorber is generally 160° C. to 210° C., preferably 170° C. to 200° C., particularly 180° C. to 195° C. The temperature is preferably established by the in-flowing melt and external heating means. The heating surfaces of the external heating means are preferably at from 165° C. to 230° C., in particular 185 to 200° C.

The quantity of gas introduced into the desorber amounts preferably to from 100 to 300 m$^3$, in particular 150–250 m$^3$, per m$^3$ of BPA/phenol adduct mixture.

The gas is preferably adjusted by preheating to temperatures above 160° C. to 230° C., in particular to temperatures of 185 to 200° C., prior to entry into the desorber.

The gases introduced are inert, preferably oxygen-free gases, in particular nitrogen. The gas is preferably recirculated after desorption by cooling and separation of the phenol. To this end, the gas is preferably scrubbed and cleaned by filtration. A quantity of gas of approximately 1–5% is preferably discharged from the recirculated stream.

The gas in the recirculated stream should preferably have an oxygen content of below 10 ppm, preferably 3 ppm, particularly preferably 1 ppm.

Abraded metallic and ceramic solid material is preferably removed from the recirculated gas stream in sintered filter cartridges.

Cooling of the gas (optionally incl. phenol injection) proceeds in such a way that product which may co-evaporate in the cooled gas stream is not deposited on the cooler surface of the condenser and the apparatus, piping and measuring means installed downstream.

The melt flow to and from the desorber is preferably filtered.

The level in the desorber is preferably set at 10–15 cm above the inlet and the packing.

The gas is preferably conveyed through a desorber filled with packing via distributor tubes and nozzles open at the bottom in counterflow to the melt flowing from top to bottom.

The number of nozzles in the distributor tubes amounts to preferably 800 to 1500 per m$^2$ of cross-sectional area.

An excess pressure of 15 to 25 mbar is preferably established at the top of the desorber.

The residence time of the product melt in the desorber amounts preferably to less than 30 mins.

The invention further provides a device for separating bis(4-hydroxyaryl)alkanes and aromatic hydroxy compounds from bis(4-hydroxyaryl)alkane/arylhydroxy adducts, characterised by a desorber, which contains tube bundle heat exchangers and wherein the spaces between the heat exchanger tubes are filled on the product side with ceramic spheres (steatite) and the product chamber is mainly filled with liquid and wherein the heat exchangers are arranged upright and provided at their lower part with a number of nozzles, via which a hot inert gas, in particular nitrogen, may be introduced, having a means for diverting the phenol, once distilled off, and the gas to a condenser and a phenol collecting receiver connected thereto, together with a scrubbing tower connected to the phenol collecting receiver and optionally filters for cleaning the gas leaving the condensers and separators and a means of returning the gas to the desorber.

In FIG. 1, the reference numerals denote as follows:
(1) desorber
(2) cooler
(3) phenol outlet
(4) gas scrubbing tower
(5) filter
(6) heating means
(7) mixed crystal introduction unit
(8) product removal unit
(9) heater
(10) gas discharge
(11) scrubbing water inlet
(12) scrubbing water outlet The following Examples serve to explain the invention. The invention is not limited to the Examples. Where not otherwise indicated, percentages stand for percentages by weight.

EXAMPLE

Example 1

The BPA/phenol adduct crystals arising during the acid-catalysed reaction of phenol and acetone with subsequent suspension crystallisation are separated off from the liquid phase by a rotary filter and cleaned and fed to a separation unit for separating BPA from phenol. To this end, a mixed crystal melt with a phenol content of 15% is pumped into a desorber (1). The temperature of the melt in the desorber is adjusted to 190° C. by melt feed and heating, wherein the temperature of the heating surfaces amounts to 200° C.

For the purpose of desorption, nitrogen (N$_2$) is introduced, wherein the amount of nitrogen amounts to 200 m$^3$/m$^3$ of BPA/phenol mixture and the N$_2$ temperature is adjusted to 195° C. by preheating prior to entry into the desorber. After desorption by cooling and separation of the phenol, the nitrogen is recirculated, scrubbed and cleaned of BPA or BPA phenol sublimate by filtration. In relation to the recirculated stream, an amount of 3% of N$_2$ is discharged.

The nitrogen is conveyed through a desorber filled with packing via distributor tubes and nozzles open at the bottom in counterflow to the melt flowing from top to bottom, wherein the number of nozzles per m² cross-sectional area amounts to approximately 1100. An excess pressure of approximately 20 mbar is preferably established at the top of the desorber and the level in the desorber is set at 15 cm above the inlet and the packing.

To achieve a high BPA quality, it must he ensured that the oxygen content in the recirculated nitrogen is below 1 ppm and abraded metallic and ceramic solid material is removed from the recirculated nitrogen in sintered filter cartridges, and that the melt flow to and from the desorber is filtered. Furthermore, the residence time of the product melt in the desorber unit should amount to <30 mins.

In this way, a BPA is obtained which exhibits a high level of purity (>99.5%) and low phenol contents (<50 ppm).

What is claimed is:

1. A process for separating bis(4-hydroxyaryl)-alkanes from adducts of bis(4-hydroxyaryl)alkanes having aromatic hydroxy compounds, which is characterised in that the crystallised, filtered-off and purified bis(4-hydroxyaryl) alkane/arylhydroxy adducts) arising during the acid catalyzed reaction of aromatic hydroxy compounds with ketones are melted under product-protective conditions and separated by desorption of the aromatic hydroxy compounds said desorption by nitrogen gas.

2. A process according to claim 1, characterised in that 2,2-bis(4-hydroxyphenyl)propane is separated from 2,2-bis(4-hydroxyphenyl)propane/phenol adducts.

3. A process according to claim 2, characterised in that the quantity of gas introduced into the desorber amounts preferably to from 100 to 300 m³ per m³ of BPA/phenol adduct mixture and the gas temperature is above 160° C. to 230° C.

4. A process according to claim 1, characterised in that the nitrogen is recirculated after desorption by cooling and separation of the phenol.

5. A device for separating bis(4-hydroxyaryl)alkanes and aromatic hydroxy compounds from bis(4-hydroxyaryl) alkane/arylhydroxy adducts arising from the acid-catalyzed reaction of aromatic compounds with ketones, characterised by a desorber (1), which contains tube bundle heat exchangers and wherein the spaces between the heat exchanger tubes are filled on the product side with ceramic spheres and the product chamber is mainly filled with liquid and wherein the heat exchangers are arranged upright and provided at their lower part with a number of nozzles, via which a hot inert gas may be introduced, having a means for diverting the phenol, once distilled off, and the gas to a condenser (2) and a phenol collecting receiver (3) connected thereto, together with a scrubbing tower (4) connected to the phenol collecting receiver and optionally filters (5) for cleaning the gas leaving the condensers (2) and separators (3) and a means of returning the gas to the desorber (1).

6. The process of claim 4 wherein 1–5% of the gas is discharged from the recirculated stream.

7. The process of claim 1 wherein the desorption is preceded by distillation.

* * * * *